US012567555B2

(12) United States Patent
Ahmed et al.

(10) Patent No.: US 12,567,555 B2
(45) Date of Patent: Mar. 3, 2026

(54) HIGH DOSE RATE RADIOTHERAPY SYSTEMS AND TARGETS

(71) Applicant: Varian Medical Systems, Inc., Palo Alto, CA (US)

(72) Inventors: Md Ahmed, East Palo Alto, CA (US); Joshua McNeur, Palo Alto, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 200 days.

(21) Appl. No.: 18/501,551

(22) Filed: Nov. 3, 2023

(65) Prior Publication Data

US 2025/0149286 A1 May 8, 2025

(51) Int. Cl.
| | |
|---|---|
| *H01J 35/00* | (2006.01) |
| *A61N 5/10* | (2006.01) |
| *H01J 35/14* | (2006.01) |

(52) U.S. Cl.
CPC .......... *H01J 35/147* (2019.05); *A61N 5/1045* (2013.01); *H01J 35/153* (2019.05); *A61N 2005/1091* (2013.01); *H01J 2235/1204* (2013.01)

(58) Field of Classification Search
CPC ........... A61B 5/1045; A61B 2005/1091; H01J 35/147; H01J 35/153; H01J 2235/1204
See application file for complete search history.

(56) References Cited

U.S. PATENT DOCUMENTS

| | | | | |
|---|---|---|---|---|
| 6,463,123 | B1* | 10/2002 | Korenev | .................. H05H 6/00 378/68 |
| 9,715,989 | B2 | 7/2017 | Dalakos et al. | |
| 2010/0201240 | A1 | 8/2010 | Heinke et al. | |
| 2016/0300686 | A1 | 10/2016 | Dalakos et al. | |
| 2023/0215680 | A1* | 7/2023 | He | .......................... H01J 35/12 378/143 |
| 2023/0293909 | A1 | 9/2023 | Clayton | |

FOREIGN PATENT DOCUMENTS

| | | |
|---|---|---|
| DE | 60101855 T2 | 11/2004 |

* cited by examiner

*Primary Examiner* — Mark R Gaworecki
(74) *Attorney, Agent, or Firm* — Harness, Dickey & Pierce, P.L.C.

(57) ABSTRACT

A radiation system includes an X-ray target configured to convert an electron beam into an X-ray beam. The X-ray target includes a plurality of target layers and each of the plurality of target layers are configured to convert a portion of the electron beam into a portion of the X-ray beam.

20 Claims, 8 Drawing Sheets

HIGH DOSE RATE RADIOTHERAPY SYSTEMS AND TARGETS

TECHNICAL FIELD

One or more example embodiments relate to targets and/or radiotherapy systems including the same.

BACKGROUND

External beam radiation therapy may be used in the treatment of various cancers and non-malignant conditions. Generally, ionizing radiation, including, for example, photons, e.g., X-rays, gamma rays, and charged particles, e.g., protons and electrons, is directed at an area of interest. In many cases, such ionizing radiation is generated by a linear accelerator or a cyclotron.

Ultra-high dose rate (UHDR) radiotherapy is an emerging radiotherapy regime that appears to reduce radiation-induced toxicities while maintaining a tumor response similar to that of more conventional radiotherapy regimes-known as FLASH effect. UHDR radiotherapy may be characterized as delivering a high radiation rate, e.g., greater than about 40 Grays (Gy) per second, that allows for a total radiotherapy treatment dose, or large fractions of a total radiation dose, to be delivered in parts of a second, compared to several minutes for conventional radiotherapy. For example, a conventional radiotherapy treatment may include a total dose of 12-25 grays (Gy) delivered at a rate of up to 0.4 Gy/s, requiring minutes of treatment time. In contrast, UHDR radiotherapy may deliver a similar total dose at a rate of 40 Gy/s, requiring a fraction of a second of treatment time.

However, generating such high dosage radiotherapy uses an increase in instantaneous dose rates of several orders of magnitude in comparison to conventional instantaneous dose rates. For example, an instantaneous dose rate of UHDR radiotherapy may be 100 times or more higher than an instantaneous dose rate used in conventional radiotherapy. For FLASH photon (X-ray) radiotherapy, this uses corresponding increases in the electron currents impacting an X-ray target.

SUMMARY

The scope of protection sought for various example embodiments is set out by the independent claims. The example embodiments and/or features, if any, described in this specification that do not fall under the scope of the independent claims are to be interpreted as examples useful for understanding various embodiments.

Independent of the grammatical term usage, individuals with male, female or other gender identities are included within the term.

Unfortunately, conventional X-ray targets and associated components are not suitable for the large currents and/or instantaneous dose rates characteristic of UHDR radiotherapy. For example, if exposed to the high beam currents and/or instantaneous dose rates characteristic of UHDR radiotherapy, conventional X-ray targets may deteriorate and/or be destroyed.

According to at least one example embodiment, a radiation system includes an X-ray target configured to convert an electron beam into an X-ray beam. The X-ray target includes a plurality of target layers and each of the plurality of target layers are configured to convert a portion of the electron beam into a portion of the X-ray beam.

BRIEF DESCRIPTION OF THE DRAWINGS

Example embodiments will become more fully understood from the detailed description given herein below and the accompanying drawings, wherein like elements are represented by like reference numerals, which are given by way of illustration only and thus are not limiting of this disclosure.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment and should not be interpreted as defining or limiting the range of values or properties encompassed by example embodiments. The use of similar or identical reference numbers in the various drawings is intended to indicate the presence of a similar or identical element or feature.

DETAILED DESCRIPTION

Various example embodiments will now be described more fully with reference to the accompanying drawings in which some example embodiments are shown.

Detailed illustrative embodiments are disclosed herein. However, specific structural and functional details disclosed herein are merely representative for purposes of describing example embodiments. The example embodiments may, however, be embodied in many alternate forms and should not be construed as limited to only the embodiments set forth herein.

It should be understood that there is no intent to limit example embodiments to the particular forms disclosed. On the contrary, example embodiments are to cover all modifications, equivalents, and alternatives falling within the scope of this disclosure. Like numbers refer to like elements throughout the description of the figures.

As discussed herein the terminology "one or more" and "at least one" may be used interchangeably.

It will be appreciated that a number of example embodiments may be used in combination.

Although one or more example embodiments may be discussed herein with regard to an embodiment of an X-ray target positioned in a treatment head of a radiotherapy system, it should be understood that example embodiments should not be limited to such examples. Rather, an X-ray target described may also be deployed as an accessory to the treatment head.

Figure 1:
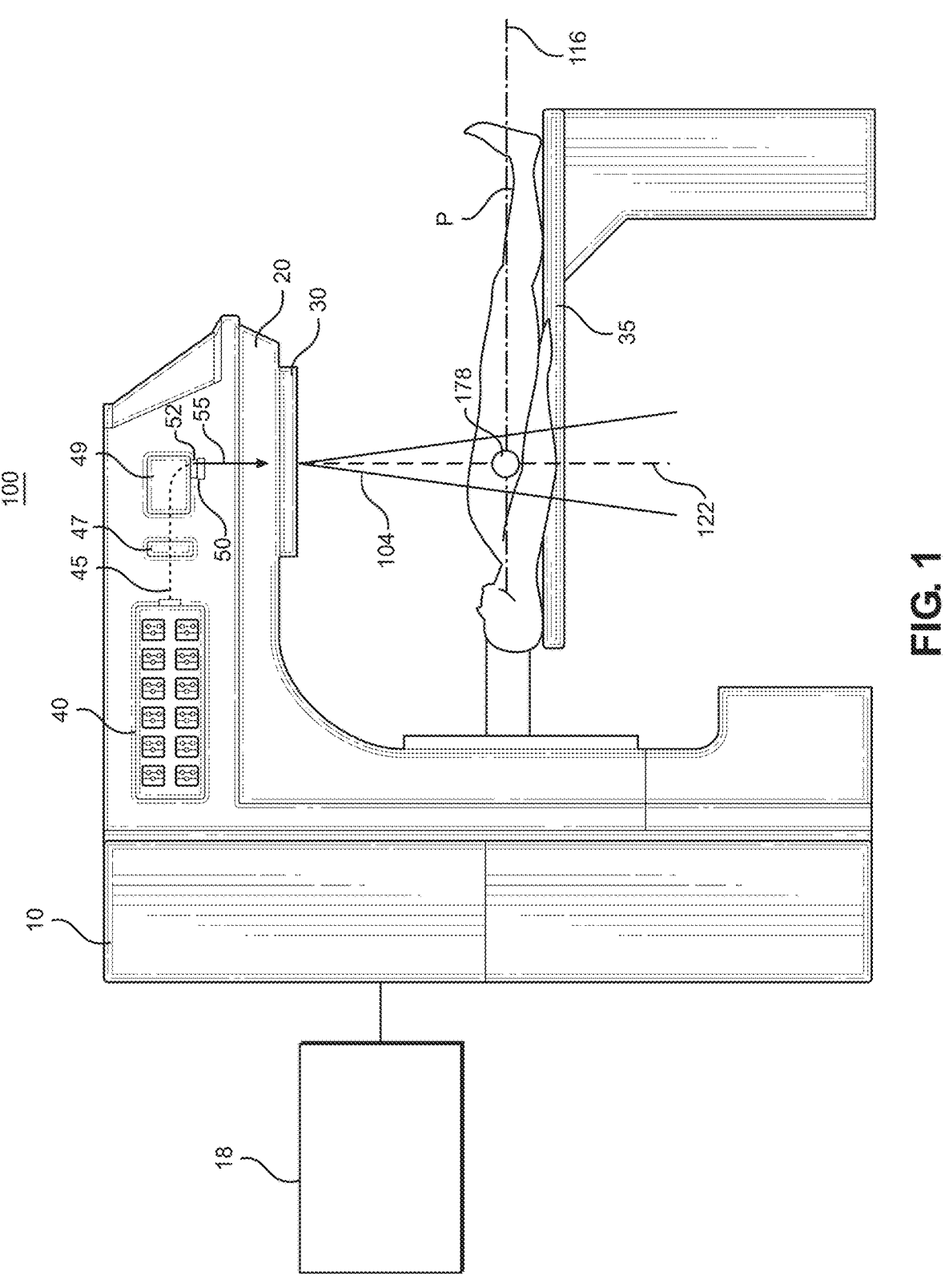
FIG. 1 illustrates a block diagram of a radiation treatment system in accordance with example embodiments.

FIG. 1 illustrates a block diagram of a radiation treatment system in accordance with example embodiments.

FIG. 1 illustrates a block diagram of an exemplary radiation treatment system 100 that may serve as a platform for example embodiments. Radiation treatment system 100 may be similar to a TrueBeam® radiotherapy system, commercially available from Varian Medical Systems, Palo Alto, CA.

A stand 10 supports a rotatable gantry 20 with a treatment head 30. The treatment head 30 may extend into the gantry 20. In proximity to the stand 10 there is arranged a control unit 18 which includes control circuitry for controlling the different modes of operation of the system 100.

The radiation treatment system 100 comprises a linear accelerator 40, for example, within the gantry 20, utilized to create a radiation beam. Typically, the radiation treatment system 100 is capable of generating either an electron (particle) beam or an X-ray (photon) beam for use in the radiotherapy treatment of patients on a treatment couch 35. Other radiation treatment systems are capable of generating light ion particles such as protons, alpha particles, or carbon ions. For purposes of the following disclosure, only X-ray (photon) irradiation will be discussed.

A high voltage source is provided within the stand and/or in the gantry to supply voltage to an electron gun (not shown) positioned on an accelerator guide located in the gantry 20. Electrons are emitted from the electron gun into the accelerator 40 where they are accelerated. A source supplies radio frequency (microwave) power for the generation of an electric field within the waveguide. The electrons emitted from the electron gun are accelerated in the waveguide by the electric field, and exit the waveguide as a high-energy electron beam 45, for example, at megavoltage energies. The electron beam 45 may pass through a set of bending plane scan magnets 47, in some embodiments. The electron beam 45 may pass through a set of bend magnets 49, to redirect the electron beam 45 from substantially horizontal to substantially vertical, in some embodiments. The electron beam 45 then enters a drift tube 52 and strikes a suitable X-ray target 50, for example, a bremsstrahlung transmission target, converting a portion of the electron beam 45 into X-rays (photons) 55 in the direction of a patient P. The drift tube 52 reduces scattering before striking the target 50 and effectively reduces a source to surface distance (SSD) between a treatment surface and the target 50. The SSD may be measured from a top of the target 50, a middle of the target 50, a bottom of the target 50 or any other location in the target 50.

As illustrated in FIG. 1, a patient P is shown lying on the treatment couch 35. High energy photons as described above are emitted from the treatment head 30 in a divergent beam 104. Typically, a patient plane 116, is positioned, for example, about one meter from the X-ray source, and the rotational axis of the gantry 20 is located on the patient plane 116, such that the distance between the target 50 and the isocenter 178 remains constant when the gantry 20 is rotated. It is appreciated that for photon FLASH therapy, the patient plane 116 may be less than one meter from the electron source. The isocenter 178 is at the intersection between the axis of rotation of the gantry 20 and the central axis of beam 122. A treatment volume to be irradiated may be located about the isocenter 178, or in some embodiments may be located closer to or farther from the treatment head 30. It is appreciated that some treatment plans may utilize a primary treatment target that is off of the central beam axis, and such arrangements are within the scope of example embodiments.

Figure 2:
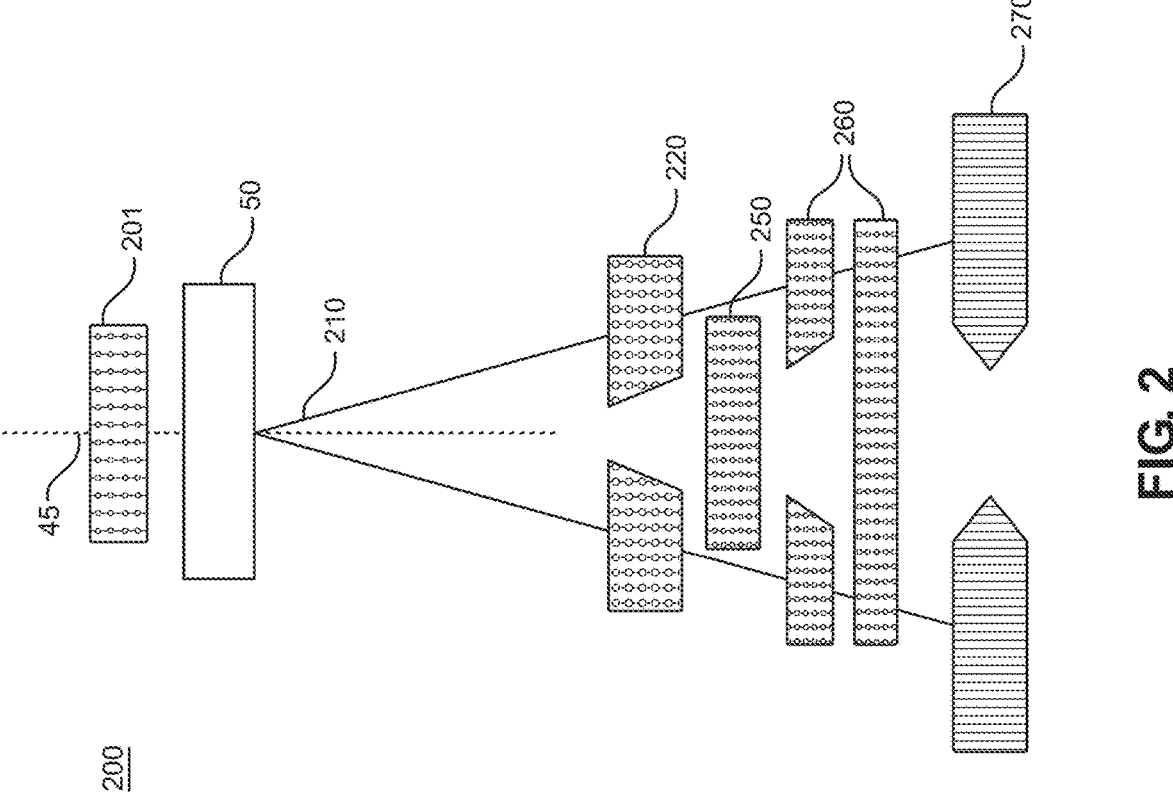
FIG. 2 illustrates a side-sectional schematic representation of an exemplary beam path in the radiation treatment system of FIG. 1, in accordance with example embodiments.

FIG. 2 illustrates a side-sectional schematic representation of an exemplary beam path 200 within the radiation treatment system 100, in accordance with example embodiments. It is appreciated that the illustrated components of the beam path 200 are exemplary, and all may not be required in some embodiments. Additional components, e.g., a flattening filter (not shown), may also be included in accordance with embodiments of the present invention. Prior to impinging the X-ray target 50, the electron beam 45 may pass through a set of cross plane scanning magnets 201, in some embodiments. As previously presented, the electron beam 45 impinges on the X-ray target 50 producing the X-ray radiation beam 210.

The radiation beam 210 passes through a monitor chamber 250, sometimes known or referred to as an "ion chamber." The monitor chamber 250 functions to measure a radiotherapy dose. X and Y jaws 260, and leaves of a multi-leaf collimator (MLC) 270 function to shape radiation beam 210 to a desired shape and/or beam profile for patient treatment.

A primary collimator 220 may comprise a plurality of selectable collimators and/or filters, in some embodiments. The primary collimator 220, typically comprises an X-ray blocking material, and may be positioned in the head 30 (FIG. 1) to define the width of the X-ray beam at the patient plane. Typically, the X and Y jaws 260 are moveable and, when fully open, define a maximum beam width at the patient plane 116 (FIG. 1). The MLC 270 may be positioned at the exit of the head 30, to further shape the X-ray beam. Exemplary MLCs may use up to 120 individually controllable leaves, for example, thin slices of tungsten, which may be moved into or out of the X-ray beam under the control of system software.

As a high-energy electron beam, e.g., 22 MeV passes through an X-ray target, e.g., Tungsten (W) or Tantalum (Ta), the linear energy transfer (LET) dictates the heat generation profile within the target. LET refers to the energy that an ionizing particle transfers to the material per unit distance traveled. As the electron beam penetrates deeper into the target material, the LET gradually increases, reaching a maximum at a critical thickness. Beyond this critical thickness, the stopping power becomes excessively high, leading to a rapid absorption of beam energy. For 22 MeV for example, the critical thickness for W/Ta is approximately 1.15 mm.

The X-ray target 50 is designed to include multiple thin layers of spatially separated targets ensuring (i) thickness of individual target layers is much smaller than the critical thickness and ii) 99% of the incident electrons lose all of their energy (are absorbed) in the X-ray target 50.

In accordance with example embodiments, the X-ray target 50 is configured to operate in UHDR radiotherapy and absorb >99% of the incident electrons. In accordance with other example embodiments, the X-ray target 50 is also configured to operate in ultra-high dose rate (UHDR) radiotherapy, e.g., at least 1 Gray (Gy) per second and absorb >99% of the incident electrons.

Figure 3A:
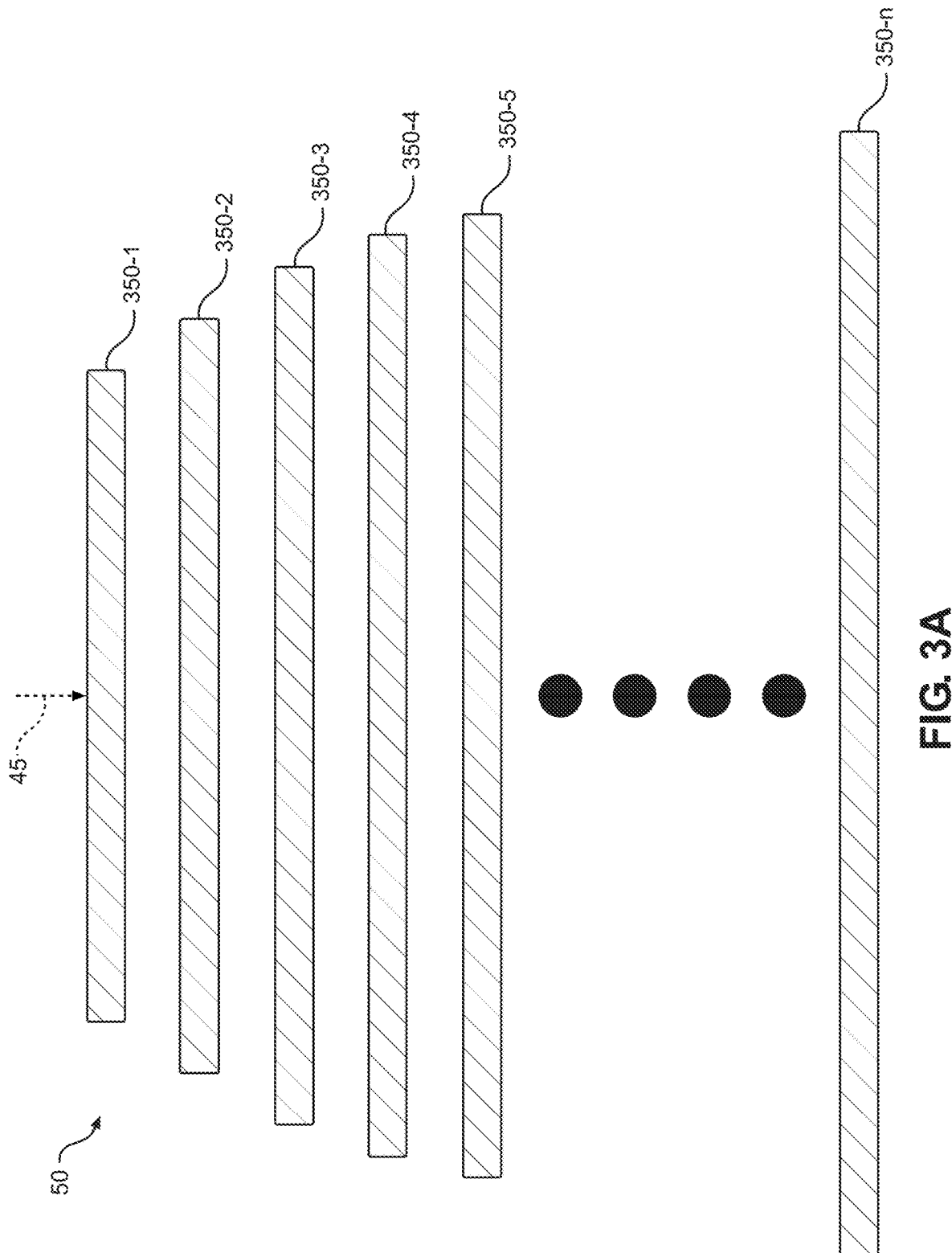
FIG. 3A illustrates a side view of an X-ray target according to one or more example embodiments.

FIG. 3A illustrates a side view of an X-ray target according to one or more example embodiments.

As shown in FIG. 3A, the X-ray target 50 includes a plurality of target layers 350-1 to 350-n. Each of the plurality of target layers 350-1 to 350-n is configured to convert a portion of the electron beam 45 into a portion of the radiation beam 210.

In some example embodiments, the plurality of target layers 350-1 to 350-n are stacked in series, e.g., along the central axis of the beam 122. However, example embodiments are not limited thereto. Moreover, the plurality of target layers 350-1 to 350-$n$ may be separated by a same distance or varying distances. For example, a first distance between the target layer 350-1 and the target layer 350-2 may be different than a second distance between the target layer 350-2 and the target layer 350-3.

The target layers 350-1 to 350-$n$ may be of the same thickness or different thicknesses. Each of the target layers 350-1 to 350-$n$ is relatively thin and comprises refractory metals. Refractory metals are characterized as a high Z materials, e.g., materials comprising elements with a high atomic number ("Z") of protons in the nucleus, and having a high melting temperature. As used herein, "high-Z" refers to or describes elements having an atomic number of 42, corresponding to molybdenum (Mo), or greater. Exemplary elements include tungsten (W), tantalum (Ta), molybdenum (Mo), gold (Au), and/or antimony (Sb). The total thickness of the target layers 350-1 to 350-$n$ is selected to be sufficient to generate the required dose of X-rays, while minimizing attenuation and energy loss of the incident high-energy electrons.

In some example embodiments, each of the target layers 350-1 to 350-$n$ is 0.1 mm for an X-ray target 50 comprising Tantalum (Ta) or Tungsten (W). In some example embodiments, each of the target layers 350-1 to 350-$n$ may be the same material.

In some example embodiments, the total thickness of the target layers 350-1 to 350-$n$ may be the same thickness as a single piece target such as 6.5 mm for an X-ray target 50 comprising Ta. In some example embodiments, each of the target layers 350-1 to 350-$n$ includes Ta and each of the target layers 350-1 to 350-$n$ may be a Ta foil.

For example, an exemplary UHDR radiotherapy treatment may require an electron energy of at least 50 MeV, producing up to 25 kW of average beam power.

As attenuation of high-energy electrons within the X-ray target 50 produces heat, separating the X-ray target 50 into layers separates electron among the target layers 350-1 to 350-$n$ and the spacing between the target layers 350-1 to 350-$n$ absorbs heat from the X-ray target 50 must endure and/or be removed from X-ray target 50. Reducing heating of the X-ray target 50 improves the stability and reliability of a UHDR radiotherapy system.

In some example embodiments, while the total thickness of the target layers 350-1 to 350-$n$ may be the same thickness as a single piece target, the spacing of the target layers 350-1 to 350-$n$ in series along the electron beam path allows for heat management through at least one of heat sinks, air cooling, radiative transfer, or (high-pressure) water cooling. For example, the target 50 may be used with the cooling system described in U.S. Pat. No. 8,761,347, the entire contents of which are incorporated by reference. The spacing of the target layers 350-1 to 350-$n$ can be paired with existing heat management solutions involving a moving target or scanning beam such as described in U.S. application Ser. No. 17/709,060, the entire contents of which are incorporated by reference. Moreover, by maintaining the total thickness of the target layers 350-1 to 350-$n$ to be the same as a single piece target, the electrons are stopped within the target, resulting in no need for additional electron contamination management. In addition, by maintaining total thickness of the target layers 350-1 to 350-$n$ to be the same as a single piece target, no extra requirements for scanning control of the electron beam are needed, nor management of a rotating (or otherwise moving) target is needed.

In example embodiments, target layers may be added or removed based on an energy level of the beam 45.

Figure 3B:
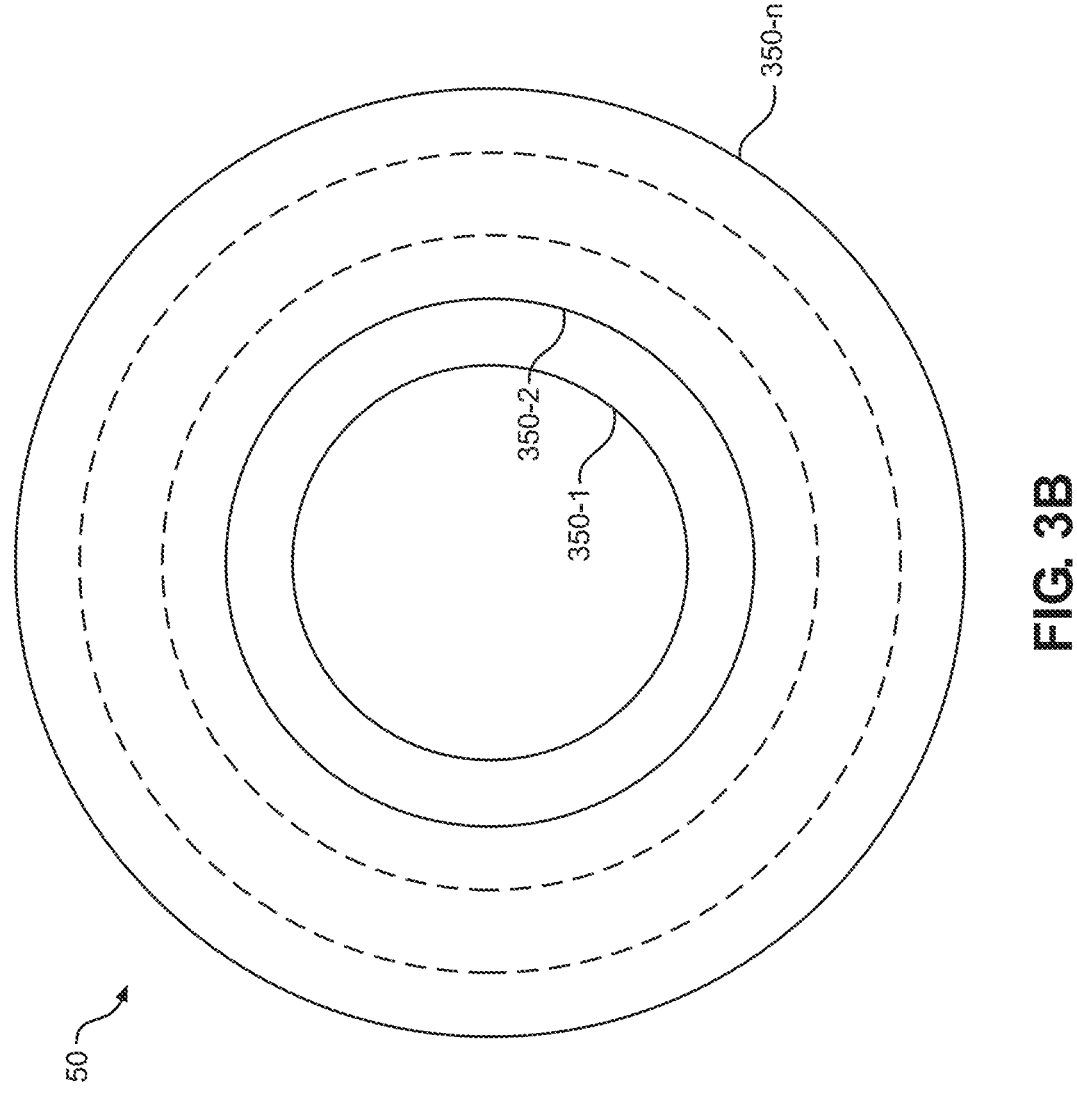
FIG. 3B illustrates a top view of an X-ray target according to one or more example embodiments.

FIG. 3B illustrates a top view of an X-ray target according to one or more example embodiments. As shown in FIG. 3B, the X-ray target 50 (and each of the target layers 350-1 to 350-$n$) is circular. The size (e.g., area of a top surface) of a target layer is larger than the incident beam spot size to maximize the bremsstrahlung efficiency and avoid passage of incoming electrons without any interaction. Thus, as shown in the example embodiment of FIGS. 3A-3B, the diameters of the plurality of target layers 350-1 to 350-$n$, respectively, follow the divergence of beam spot size. More specifically, the first target layer 350-1 that is struck by the electron beam 45 has a smallest diameter among the target layers 350-1 to 350-$n$. The last target layer 350-$n$ has the largest diameter among the target layers 350-1 to 350-$n$ and each of the remaining target layers 350-2 to 350-$n$-1 has a diameter that is larger that a preceding target layer (along the direction of the electron beam 45) and smaller than a subsequent target layer (along the direction of the electron beam 45).

While FIGS. 3A-3B illustrate that the target layers 350-1 to 350-$n$ are circular, it should be understood that the target layers 350-1 to 350-$n$ may be another shape such triangular or rectangular.

Figure 4:
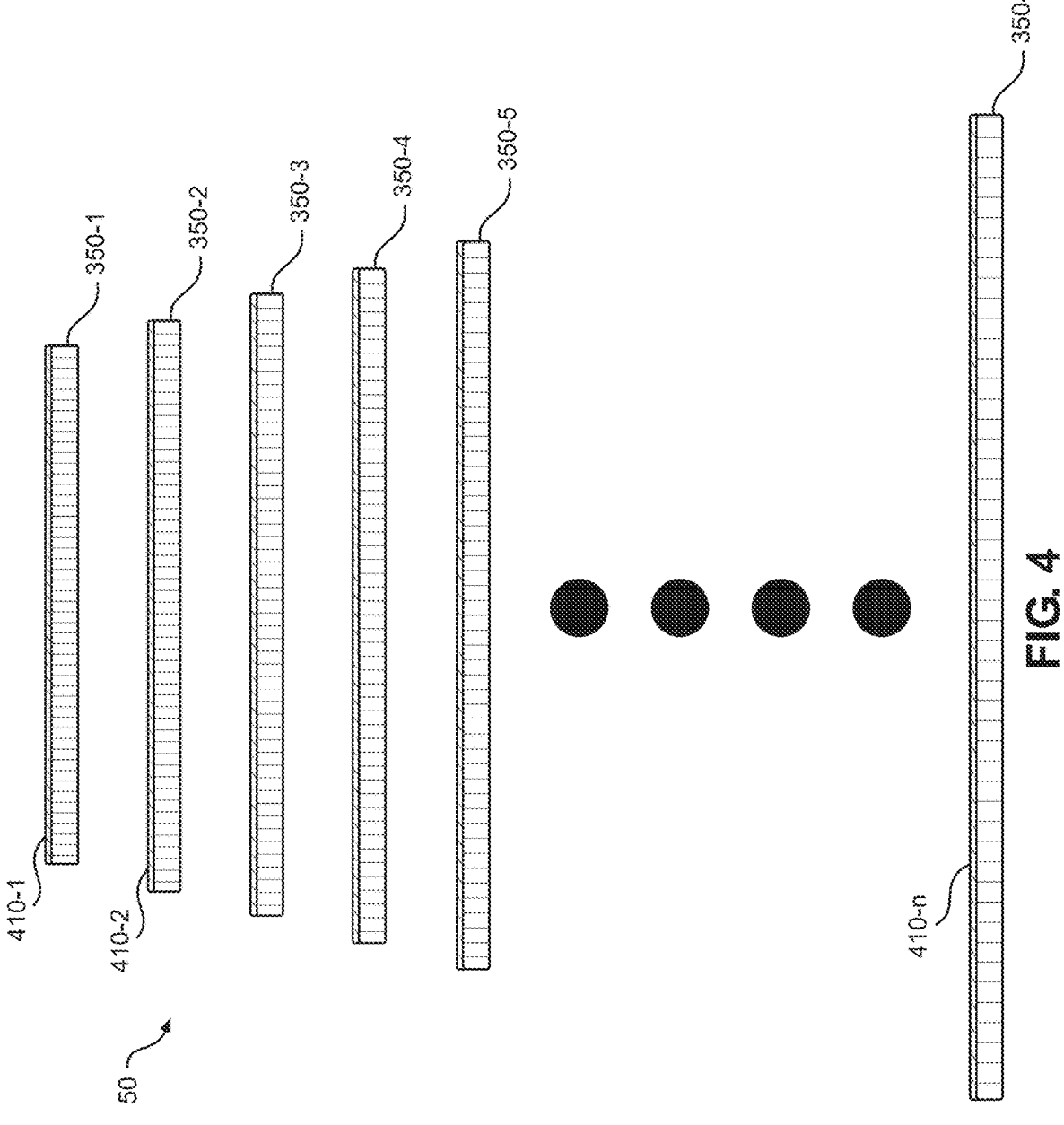
FIG. 4 illustrates a side view of an X-ray target and a heat transfer material according to one or more example embodiments.

FIG. 4 illustrates a side view of an X-ray target and a heat transfer material according to one or more example embodiments. As shown in FIG. 4, heat transfer material layers 410-1 to 410-$n$ are located on the plurality of target layers 350-1 to 350-$n$, respectively. Thus, in the example shown in FIG. 4 in layers of the heat transfer material layer 410 are in the target 50. The heat transfer material layers 410-1 to 410-$n$ may be attached to the target layers 350-1 to 350-$n$, respectively using a thermal paste or any other known way.

The thickness of the target layers 350 and the heat transfer layers 410 is not to scale. In some example embodiments, all the heat transfer layers are thicker than the target layers, in other example embodiments, all target layers are thicker than the heat transfer layers and, in other example embodiments, some heat transfer layers are thicker than the target layers. In other example embodiments, the target layers and the heater transfer layers may have the same thickness.

The heat transfer material layers 410-1 to 410-$n$ transfer and absorb heat from the plurality of target layers 350-1 to 350-$n$ to reduce heating of the X-ray target 50. The heat transfer material layers 410-1 to 410-$n$ may be copper or any other known material having a high thermal conductivity such as Diamond. Each of the heat transfer material layers 410-1 to 410-$n$ may have a thermal conductivity of at least 400 W/(m·K). In some example embodiments, the shape of each heat transfer material layer 410-1 to 410-$n$ is such that it covers a top surface of the respective target layer 350-1 to 350-$n$. As an example, when the target layer 350-1 is cylindrical/circular, the heat transfer material layer 410-1 has a diameter that is the same as the target layer 350-1. The thickness of each heat transfer material layer 410-1 to 410-$n$ may be dictated by a desired energy to be absorbed by the heat transfer material layer. In some example embodiments, the heat transfer material layer 410-1 may have a thickness greater than the other heat transfer material layers 410-2 to 410-$n$. The thickness of each heat transfer material layer may be sufficient to dissipate heat to a water channel in a same layer of the target.

Figure 5A:
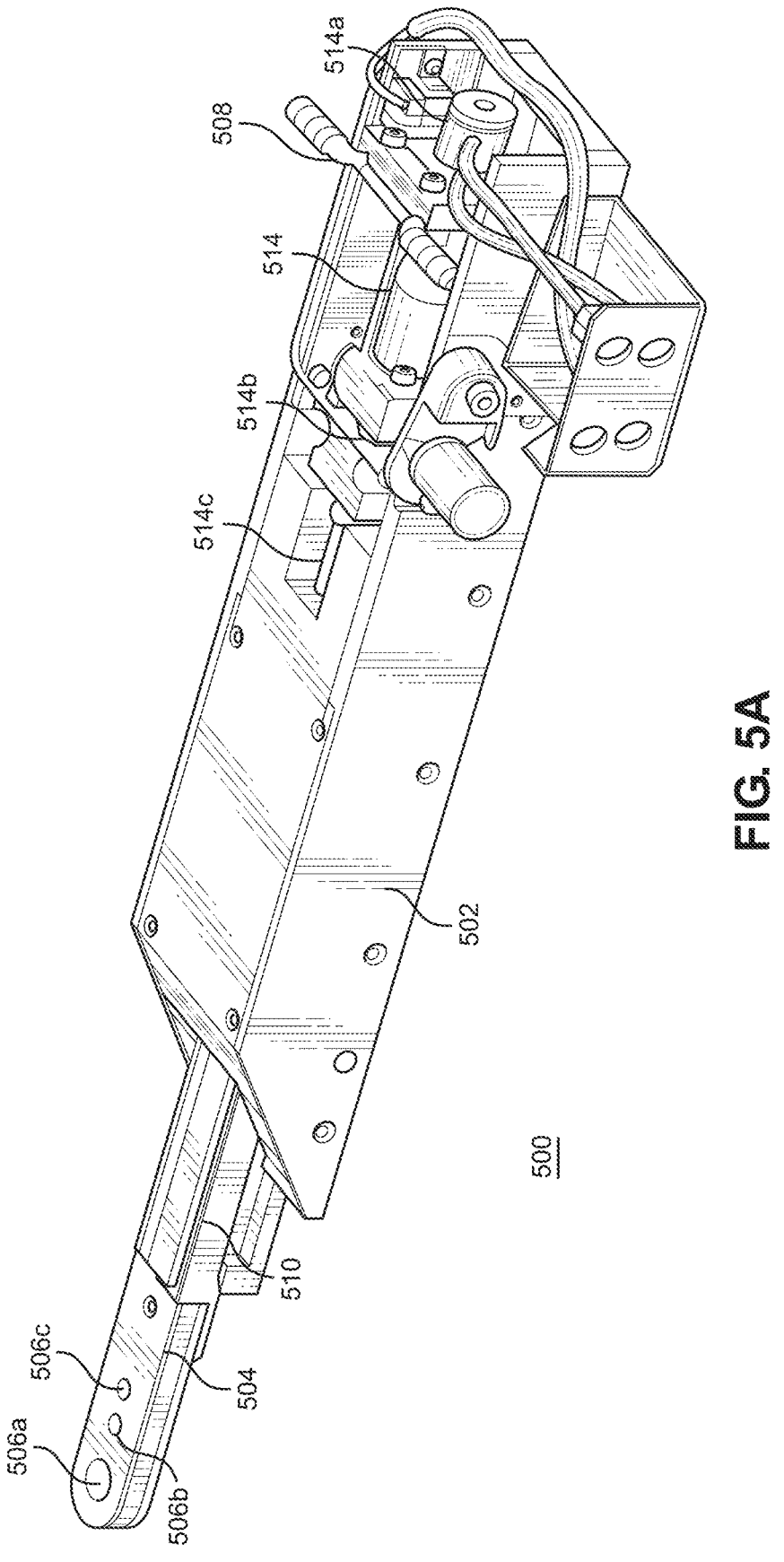
FIGS. 5A-5C illustrate a target assembly according to one or more example embodiments.

FIG. 5A is a perspective view of an exemplary target assembly 500 in accordance with some example embodiments. The target assembly 500 positions a target in the beam path for generation of X-rays in a photon mode, or moves a target out of the beam path in an electron mode. The target assembly 500 includes a channel mount 502, a substrate 504 supporting one or more target buttons 506 and a cooling tube 508 coupled to the substrate 504 for supplying a cooling fluid. At least one of the one or more targets buttons 506 may be the target 50. Channels can be provided in the substrate 504 adjacent or surrounding the target buttons 506 for circulating a cooling fluid to dissipate heat generated during target operation. The substrate 504 and the cooling tube 508 can be supported by a mount assembly 510, which is movable relative to the channel mount 502.

The target assembly 500 and cooling tube 508 are further described in U.S. Pat. No. 8,761,347, the entire contents of which are incorporated by reference.

Thus, the target 50 may be used with existing cooling mechanisms.

Figures 5B, 5C:
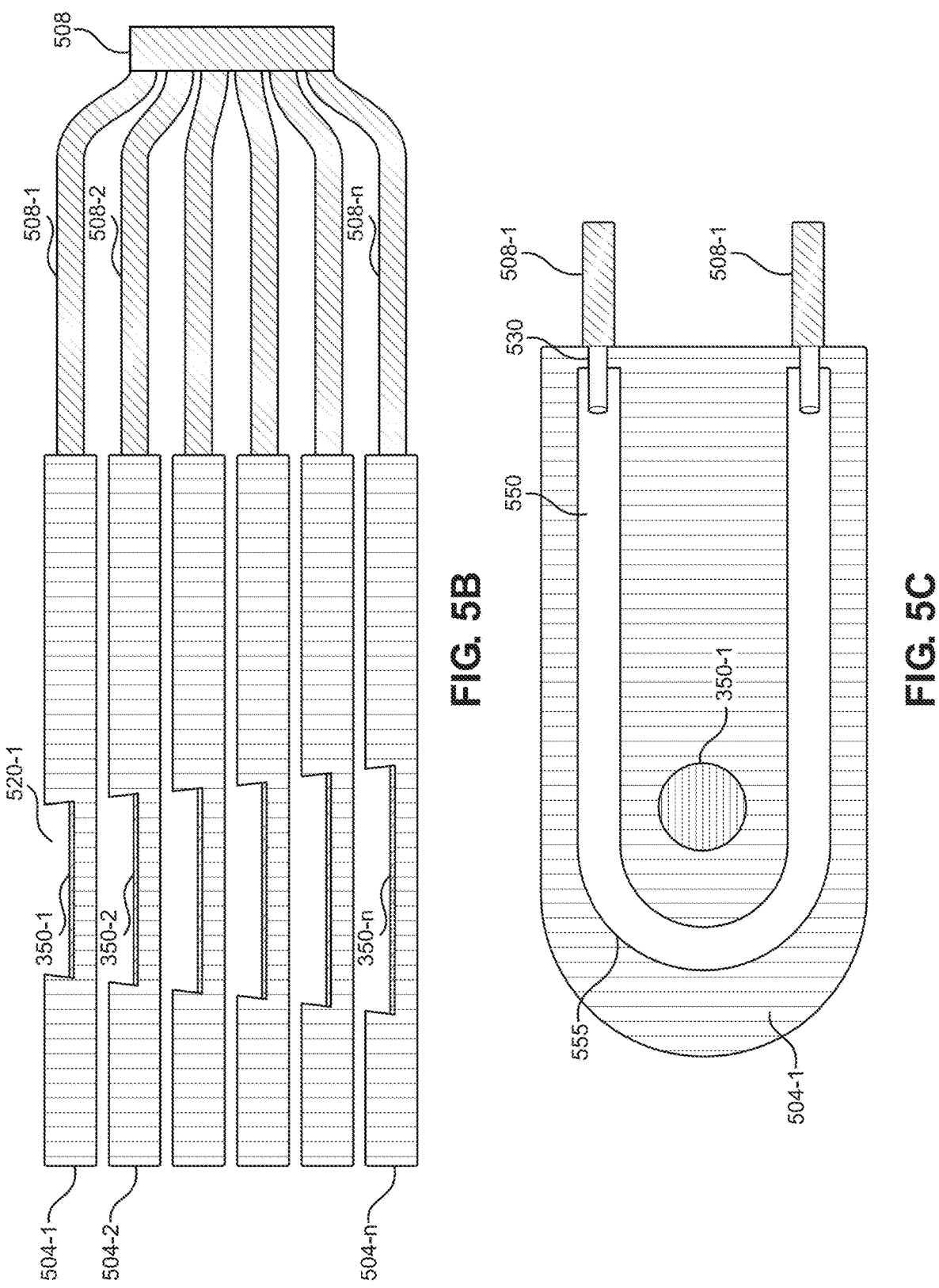

FIGS. 5B-5C illustrate at least one example embodiment using a plurality of cooling tubes. FIG. 5B illustrates a cross-sectional view of the target assembly 500. In some example embodiments, a plurality of cooling tubes 508-1 to 508-*n* may be used for the target layers 350-1 to 350-*n*, respectively, as shown in FIGS. 5B-5C.

As shown in FIG. 5B, each of the target layers 350-1 to 350-*n* is placed in a corresponding heat sink layer 504-1 to 504-*n*. More specifically, each heat sink layer 504-1 to 504-*n* has a receiving area 520 with a diameter that is the same ore slightly larger than the target layer 350 corresponding to the heat sink layer 504-1 to 504-*n*. While not illustrated in FIG. 5B, the heat transfer material layers 410-1 to 410-*n* may also be placed on the target layers 350-1 to 350-*n*, respectively. In some example embodiments, only a selected number of the heat transfer material layers may be used. For example, only the heat transfer material layer 410-1 may be used on the remaining target layers 350-2 to 350-*n* may not have a corresponding heat transfer material layer.

Each of the 1 to n layers includes a cooling tube 508.

The target assembly 500 may include a plurality of slots to accommodate a varying number of target layers. For example, the target assembly may have n slots and n cooling tubes. Based on the energy level of the beam 45, a selected number of target and heat sink layers may be inserted into the n slots. The selected number may be n or less than n. Each of the slots may have a defined mounting for a target and heat sink layer. Moreover, while the combination of a layer is described as a target and heat sink layer, it should be understood that the slots may accommodate a combination target layer and heat transfer material layer and/or a combination of the target layer, heat transfer material layer and heat sink layer.

As an example, the target assembly 500 may include five or six slots to accommodate a 22 meV beam with each target layer being a 1 mm thick layer and each heat transfer material layer being 2 mm thick.

FIG. 5C illustrates a top view (e.g., beam-eye view) of the first layer. The remaining layers are the same, with the exception of the size of the target layer within the corresponding layer.

As shown in FIG. 5C, the cooling tube 508-1 supplies water (or another cooling liquid) to a cooling channel 550 through a coupling 530. The cooling channel 550 and the coupling 530 may be embedded in the heat sink layer 504-1. The cooling channel 550 may have a general u-shape. A curved portion 555 of the U-shaped cooling channel 550 may have a curvature that matches the curvature of the target layer 350-1. However, example embodiments are not limited thereto and the cooling channel 550 may have a different shape.

Moreover, each of the couplings 530 may include valve that is operable based on whether a target and heat sink layer is being used in a slot. For example, if a target and heat sink layer is present in the slot, the valve is open to allow the flow of water through a channel in the heat sink layer. If no target and heat sink layer is present in the slot, the corresponding valve is closed.

Referring back to FIG. 5A, the target assembly 500 can be moved by a linear axis 514, which includes a motor 514*a*, a ball screw, a coupler 514*b* coupling the motor and the ball screw, and a ball nut 514*c* engaging the ball screw.

The target assembly 500 may include one or more targets each being optimized to match the energy of an incident electron beam. For example, the target assembly 500 may include a first target 506*a* adapted for a first photon mode, a second target 506*b* for a second photon mode and a third target 506*c* for a third photon mode. It should be noted that a different number of targets may be included in the target assembly 500. In operation, the linear axis 514 moves or positions one of the targets 506 in the beam path for a photon mode. In an electron mode, the linear axis 514 removes the targets 506 out of the beam path to allow an electron beam passes unimpeded.

It should be noted that a different number of targets may be included in the target assembly 500. In operation, the linear axis 514 moves or positions one of the targets 506 in the beam path for a photon mode. In an electron mode, the linear axis 514 removes the targets 506 out of the beam path to allow an electron beam passes unimpeded.

Figure 6:
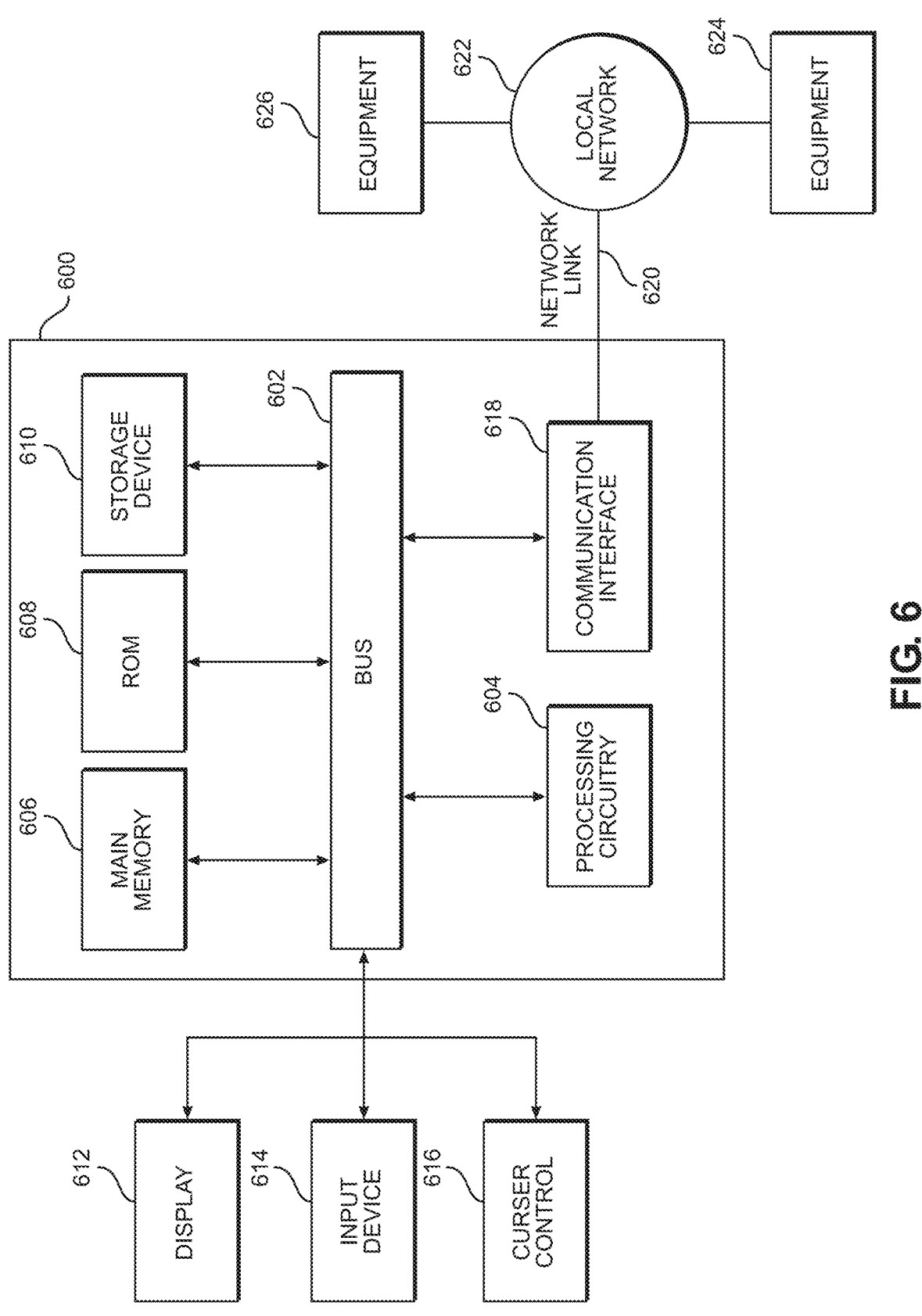
FIG. 6 illustrates a block diagram of a control system with which embodiments may be implemented.

FIG. 6 illustrates a block diagram of a control system with which embodiments may be implemented.

In some embodiments, a control system 600 shown in FIG. 6 may be used to implement the control unit 18. The control system 600 may also be an example of any control system described herein.

The control system 600 includes a bus 602 or other communication mechanism for communicating information, and processing circuitry 604 (e.g., at least one processor and/or ASIC) coupled with the bus 602 for processing information. In examples where the processing circuitry 604 is hardware configured to executed stored instructions (e.g., a processor), the control system 600 also includes a main memory 606, such as a random-access memory (RAM) or other dynamic storage device, coupled to the bus 602 for storing information and instructions to be executed by the processing circuitry 604. The main memory 106 also may be used for storing temporary variables or other intermediate information during execution of instructions to be executed by the processing circuitry 604. The control system 600 further includes a read only memory (ROM) 608 or other static storage device coupled to the bus 602 for storing static information and instructions for the processing circuitry 604. A data storage device 610, such as a magnetic disk or optical disk, may be provided and coupled to the bus 602 for storing information and instructions.

The control system 600 may be coupled via the bus 602 to a display 612, such as a flat panel, for displaying information to a user. An input/output device 614, such as a touchscreen, is coupled to the bus 602 for communicating information and command selections to processing circuitry 604. Another type of user input device is cursor control 616, such as a mouse, a trackball, or cursor direction keys for communicating direction information and command selections to processing circuitry 604 and for controlling cursor movement on display 612. This input device typically has two degrees of freedom in two axes, a first axis (e.g., x) and a second axis (e.g., y), that allows the device to specify positions in a plane.

While the display 612 and I/O device 614 are shown outside of the control system 600, it should be understood that the display 612 and the I/O device 614 are part of the control system 600. Moreover, while the display 612, the I/O device 614 and the curser control 616 are illustrated as separate components, it should be understood that they may be combined, such as a touch screen display.

In some embodiments, the control system 600 can be used to perform various functions described herein. According to some embodiments, such use is provided by control system 100 in response to the processing circuitry 604 executing one or more sequences of one or more instructions contained in the main memory 606. Those skilled in the art will know how to prepare such instructions based on the functions, algorithms and methods described herein. Such instructions may be read into the main memory 606 from another processor-readable medium, such as storage device 610. Execution of the sequences of instructions contained in the main memory 606 causes the processing circuitry 604 to perform the process steps described herein. One or more processors in a multi-processing arrangement may also be employed to execute the sequences of instructions contained in the main memory 606. In alternative embodiments, hard-wired circuitry may be used in place of or in combination with software instructions to implement the various embodiments described herein. Thus, embodiments are not limited to any specific combination of hardware circuitry and software.

Transmission media includes coaxial cables, copper wire and fiber optics, including the wires that comprise the bus 602. Transmission media can also take the form of acoustic or light waves, such as those generated during radio wave and infrared data communications.

Various forms of processor-readable media may be involved in carrying one or more sequences of one or more instructions to the processing circuitry 604 for execution. For example, the instructions may initially be carried on a magnetic disk of a remote computer. The remote computer can load the instructions into its dynamic memory and send the instructions over a network, such as the Internet or a local network. A receiving unit local to the control system 600 can receive the data from the network and provide the data on the bus 1602. The bus 602 carries the data to the main memory 606, from which the processing circuitry 604 retrieves and executes the instructions. The instructions received by the main memory 606 may optionally be stored on the storage device 610 either before or after execution by the processing circuitry 604.

The control system 600 also includes a communication interface 618 coupled to the bus 602. The communication interface 618 provides a two-way data communication coupling to a network link 620 that is connected to a local network 622. For example, the communication interface 618 may be an integrated services digital network (ISDN) card or a modem to provide a data communication connection to a corresponding type of telephone line. As another example, the communication interface 618 may be a local area network (LAN) card to provide a data communication connection to a compatible LAN. Wireless links may also be implemented. In any such implementation, the communication interface 618 sends and receives electrical, electromagnetic or optical signals that carry data streams representing various types of information.

The network link 620 typically provides data communication through one or more networks to other devices. For example, the network link 620 may provide a connection through local network 622 to a host computer 624 or to equipment 626 such as a radiation beam source or a switch operatively coupled to a radiation beam source. The data streams transported over the network link 620 can comprise electrical, electromagnetic or optical signals. The signals through the various networks and the signals on the network link 620 and through the communication interface 618, which carry data to and from the control system 600, are exemplary forms of carrier waves transporting the information. The control system 600 can send messages and receive data, including program code, through the network(s), the network link 620, and the communication interface 618.

Although the terms first, second, etc. may be used herein to describe various elements, these elements should not be limited by these terms. These terms are only used to distinguish one element from another. For example, a first element could be termed a second element, and similarly, a second element could be termed a first element, without departing from the scope of this disclosure. As used herein, the term "and/or," includes any and all combinations of one or more of the associated listed items.

When an element is referred to as being "connected," or "coupled," to another element, it can be directly connected or coupled to the other element or intervening elements may be present. By contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Specific details are provided in the following description to provide a thorough understanding of example embodiments. However, it will be understood by one of ordinary skill in the art that example embodiments may be practiced without these specific details. For example, systems may be shown in block diagrams so as not to obscure the example embodiments in unnecessary detail. In other instances, well-known processes, structures and techniques may be shown without unnecessary detail in order to avoid obscuring example embodiments.

As discussed herein, illustrative embodiments are described with reference to acts and symbolic representations of operations (e.g., in the form of flow charts, flow diagrams, data flow diagrams, structure diagrams, block diagrams, etc.) that may be implemented as program modules or functional processes include routines, programs, objects, components, data structures, etc., that perform particular tasks or implement particular abstract data types and may be implemented using existing hardware, for example, processing or control circuitry such as, but not limited to, one or more processors, one or more Central Processing Units (CPUs), one or more controllers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUS), one or more microprocessors, one or more Application Specific Integrated Circuits (ASICs), or any other device or devices capable of responding to and executing instructions in a defined manner.

Although a flow chart may describe the operations as a sequential process, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "memory," "storage medium," "processor readable medium," "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine-readable mediums for storing information. The term "computer-readable medium" may include, but is not limited to, portable or fixed storage devices, optical storage devices, and various other mediums capable of storing, containing or carrying instruction(s) and/or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, a processor or processors will perform the necessary tasks. For example, as mentioned above, according to one or more example embodiments, at least one memory may include or store computer program code, and the at least one memory and the computer program code may be configured to, with at least one processor, cause a network element or network device to perform the necessary tasks. Additionally, the processor, memory and example algorithms, encoded as computer program code, serve as means for providing or causing performance of operations discussed herein.

The terms "including" and/or "having," as used herein, are defined as comprising (i.e., open language). The term "coupled," as used herein, is defined as connected, although not necessarily directly, and not necessarily mechanically. Terminology derived from the word "indicating" (e.g., "indicates" and "indication") is intended to encompass all the various techniques available for communicating or referencing the object/information being indicated. Some, but not all, examples of techniques available for communicating or referencing the object/information being indicated include the conveyance of the object/information being indicated, the conveyance of an identifier of the object/information being indicated, the conveyance of information used to generate the object/information being indicated, the conveyance of some part or portion of the object/information being indicated, the conveyance of some derivation of the object/information being indicated, and the conveyance of some symbol representing the object/information being indicated.

Benefits, other advantages, and solutions to problems have been described above with regard to specific embodiments. However, the benefits, advantages, solutions to problems, and any element(s) that may cause or result in such benefits, advantages, or solutions, or cause such benefits, advantages, or solutions to become more pronounced are not to be construed as a critical, required, or essential feature or element of any or all the claims.

Non-Limiting Illustrative Embodiments

Illustrative embodiment 1. A radiotherapy system comprising:

an X-ray target configured to convert an electron beam into an X-ray beam, the X-ray target including, a plurality of target layers, each of the plurality of target layers configured to convert a portion of the electron beam into a portion of the X-ray beam.

Illustrative embodiment 2. The radiotherapy system of illustrative embodiment 1, wherein a diameter of each of the plurality of target layer corresponds to a divergence of a beam spot size.

Illustrative embodiment 3. The radiotherapy system of any one of illustrative embodiments 1-2, wherein the radiotherapy system is configured to control the electron beam such that the X-ray beam delivers a radiation rate of at least 40 grays per second (Gy/s).

Illustrative embodiment 4. The radiotherapy system of any one of illustrative embodiments 1-2, wherein the radiotherapy system is configured to control the electron beam such that the X-ray beam delivers a radiation rate of at least 1 gray per second (Gy/s).

Illustrative embodiment 5. The radiotherapy system of any one of illustrative embodiments 1-4, wherein the plurality of target layers are stacked in series.

Illustrative embodiment 6. The radiotherapy system of illustrative embodiment 5, wherein the plurality of target layers are separated by a same distance.

Illustrative embodiment 7. The radiotherapy system of illustrative embodiment 5, wherein a first distance between a first target layer of the plurality of target layers and a second target layer of the plurality of target layers is different than a second distance between the second target layer of the plurality of target layers and a third target layer of the plurality of target layers.

Illustrative embodiment 8. The radiotherapy system of any one of illustrative embodiments 1-7, wherein the plurality of target layers includes at least one of tantalum (Ta) or tungsten (W).

Illustrative embodiment 9. The radiotherapy system of any one of illustrative embodiments 1-8, further comprising a heat transfer material between at least two target layers of the X-ray target.

Illustrative embodiment 10. The radiotherapy system of illustrative embodiment 9, wherein the heat transfer material has a high thermal conductivity.

Illustrative embodiment 11. The radiotherapy system of any one of illustrative embodiments 9-10, wherein the heat transfer material includes copper.

Illustrative embodiment 12. The radiotherapy system of any one of illustrative embodiments 1-11, further comprising:

a plurality of heat transfer material layers associated with the plurality of target layers, respectively, each heat transfer material layer and respective target layer forming a paired layer, wherein the paired layers are spaced apart along a central axis of the electron beam.

Illustrative embodiment 13. The radiotherapy system of illustrative embodiment 12, wherein the paired layers are spaced apart equidistantly.

Illustrative embodiment 14. The radiotherapy system of any one of illustrative embodiments 1-13, further comprising:

a plurality of heat sink layers receiving the plurality of target layers, respectively, each heat sink layer and respective target layer forming a paired layer, wherein the paired layers are spaced apart along a central axis of the electron beam.

Illustrative embodiment 15. The radiotherapy system of illustrative embodiment 14, wherein each heat sink layer includes a receiving area having a size corresponding to the respective target layer.

Illustrative embodiment 16. The radiotherapy system of any one of illustrative embodiments 14-15, further comprising:

at least one cooling apparatus coupled to at least one of the paired layers and configured to supply a cooling fluid.

Illustrative embodiment 17. The radiotherapy system of illustrative embodiment 16, wherein the at least one cooling apparatus is a pipe.

Illustrative embodiment 18. The radiotherapy system of any one of illustrative embodiments 14-17, wherein the at least one paired layer defines a channel in the associated heat sink layer to receive the cooling fluid.

Illustrative embodiment 19. The radiotherapy system of any one of illustrative embodiments 1-19, wherein the X-ray target is configured to absorb at least 90% of electrons of the electron beam, the electron beam incident on the X-ray target.

Illustrative embodiment 20. The radiotherapy system of illustrative embodiment 19, wherein the X-ray target is configured to absorb at least 99% of the electrons of the incident electron beam.

Illustrative embodiment 21. The radiotherapy system of any one of illustrative embodiments 1-20, wherein a number of plurality of target layers the X-ray target is adjustable based on an energy of the electron beam.

What is claimed is:

1. A radiotherapy system comprising:

an X-ray target configured to convert an electron beam into an X-ray beam, the X-ray target including, a plurality of target layers, each of the plurality of target layers configured to convert a portion of the electron beam into a portion of the X-ray beam, wherein a diameter of each of the plurality of target layers corresponds to a divergence of beam spot size.

2. The radiotherapy system of claim 1, wherein the radiotherapy system is configured to control the electron beam such that the X-ray beam delivers a radiation rate of at least 40 grays per second (Gy/s).

3. The radiotherapy system of claim 1, wherein the radiotherapy system is configured to control the electron beam such that the X-ray beam delivers a radiation rate of at least 1 gray per second (Gy/s).

4. The radiotherapy system of claim 1, wherein the plurality of target layers are stacked in series.

5. The radiotherapy system of claim 4, wherein the plurality of target layers are separated by a same distance.

6. The radiotherapy system of claim 4, wherein a first distance between a first target layer of the plurality of target layers and a second target layer of the plurality of target layers is different than a second distance between the second target layer of the plurality of target layers and a third target layer of the plurality of target layers.

7. The radiotherapy system of claim 1, wherein the plurality of target layers includes at least one of tantalum (Ta) or tungsten (W).

8. The radiotherapy system of claim 1, further comprising:

a heat transfer material between at least two target layers of the X-ray target.

9. The radiotherapy system of claim 8, wherein the heat transfer material has a high thermal conductivity.

10. The radiotherapy system of claim 9, wherein the heat transfer material includes copper.

11. The radiotherapy system of claim 1, further comprising:

a plurality of heat transfer material layers associated with the plurality of target layers, respectively, each heat transfer material layer and respective target layer forming a paired layer, wherein the paired layers are spaced apart along a central axis of the electron beam.

12. The radiotherapy system of claim 11, wherein the paired layers are spaced apart equidistantly.

13. The radiotherapy system of claim 1, further comprising:

a plurality of heat sink layers receiving the plurality of target layers, respectively, each heat sink layer and respective target layer forming a paired layer, wherein the paired layers are spaced apart along a central axis of the electron beam.

14. The radiotherapy system of claim 13, wherein each heat sink layer includes a receiving area having a size corresponding to the respective target layer.

15. The radiotherapy system of claim 13, further comprising:

at least one cooling apparatus coupled to at least one of the paired layers and configured to supply a cooling fluid.

16. The radiotherapy system of claim 15, wherein the at least one cooling apparatus is a pipe.

17. The radiotherapy system of claim 15, wherein the at least one paired layer defines a channel in the associated heat sink layer to receive the cooling fluid.

18. The radiotherapy system of claim 1, wherein the X-ray target is configured to absorb at least 90% of electrons of the electron beam, the electron beam incident on the X-ray target.

19. The radiotherapy system of claim 18, wherein the X-ray target is configured to absorb at least 99% of the electrons of the incident electron beam.

20. The radiotherapy system of claim 19, wherein a number of plurality of target layers the X-ray target is adjustable based on an energy of the electron beam.

* * * * *